(12) United States Patent
Gangjee

(10) Patent No.: US 8,030,319 B2
(45) Date of Patent: Oct. 4, 2011

(54) METHODS FOR TREATING CANCER AND OTHER PATHOLOGICAL PROLIFERATING DISORDERS BY INHIBITING MITOSIS USING PYRROLO[2 3-D]PYRIMIDINES

(75) Inventor: Aleem Gangjee, Allison Park, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 1157 days.

(21) Appl. No.: 11/055,732

(22) Filed: Feb. 10, 2005

(65) Prior Publication Data
US 2006/0178380 A1 Aug. 10, 2006

(51) Int. Cl.
A61K 31/519 (2006.01)
A61K 31/136 (2006.01)

(52) U.S. Cl. ............. 514/265.1; 514/647; 514/183

(58) Field of Classification Search .............. None
See application file for complete search history.

(56) References Cited

U.S. PATENT DOCUMENTS

| | | |
|---|---|---|
| 5,196,424 A | 3/1993 | Gossett et al. |
| 5,346,900 A | 9/1994 | Gangjee |
| 5,508,281 A | 4/1996 | Gangjee |
| 5,736,547 A | 4/1998 | Gangjee |
| 5,863,920 A | 1/1999 | Gangjee |
| 5,866,580 A | 2/1999 | Gangjee |
| 5,877,178 A | 3/1999 | Gangjee |
| 5,939,420 A | 8/1999 | Gangjee |
| 5,958,930 A | 9/1999 | Gangjee |
| 6,077,844 A | 6/2000 | Gangjee |
| 6,096,750 A | 8/2000 | Gangjee |
| 6,103,727 A | 8/2000 | Gangjee |
| 6,114,339 A | 9/2000 | Gangjee |
| 6,221,872 B1 | 4/2001 | Gangjee |
| 6,420,370 B1 | 7/2002 | Gangjee |
| 6,423,720 B1 | 7/2002 | Gangjee |
| 6,518,426 B1 | 2/2003 | Gangjee |
| 6,696,455 B1 | 2/2004 | Gangjee |
| 6,770,652 B2 | 8/2004 | Gangjee |

FOREIGN PATENT DOCUMENTS
WO WO 03/032911 A2 4/2003

OTHER PUBLICATIONS

Parimoo et al., Cancer Control: Journal of the Moffitt Cancer Center, 2000, vol. 7(4), pp. 1-11 of 11, downloaded from "http://www.medscape.com/viewarticle/408998" on Apr. 24, 2009.*
U.S. Appl. No. 10/384,686, A. Gangjee.
U.S. Appl. No. 10/185,562, A. Gangjee.
Aleem Gangjee, Jianming Yu, Roy L. Kisliuk, William H. Haile, Giula Sobrero, and John J. McGuire, Design, Synthesis, a Biological Activities of Classical N-(4-[2-(2-Amino-4-ethylpyrrolo[2,3,-d] pyrimidin-5-yl)ethyl]benzoyl)-L-glutamic Acid and Its 6-Methyl Derivative Potential Dual Inhibitors of Thymidylate Synthase and Dihydrofolate Reductase and as Potential Antitumor Agents, *J. Medical Chemistry 2003*, 46, 591-600, Division of Medicinal Chemistry, Graduate School of Pharmaceutical Services, Duquesne University, Pittsburgh, Pennsylvania 15282.
Aleem Gangjee, Jianming Yu, John J. McGuire, Vivian Cody, Nikolai Galitsky, Roy L. Kisliuk, and Sherry P Queener, Design, Synthesis, and X-Ray Crystal Structure of a Potential Dual Inhibitor of Thymidylate Synthase and Dihydrofole Reductase as an Antitumor Agent, *J. Medical Chemistry 2000*, 43 3837, pp. 3837-3851, Division of Medicinal Chemistry, Graduate School of Pharmaceutical Sciences, Duquesne University, Pittsburgh, Pennsylvania 15282.

* cited by examiner

Primary Examiner — James Anderson
Assistant Examiner — Gregg Polansky
(74) Attorney, Agent, or Firm — Craig G. Cochenour; Buchanan Ingersoll & Rooney PC

(57) ABSTRACT

The present invention provides methods for treating cancer and other pathological proliferating conditions by inhibiting mitosis using at least one pyrrolo[2,3-d]pyrimidine having the general formula (16):

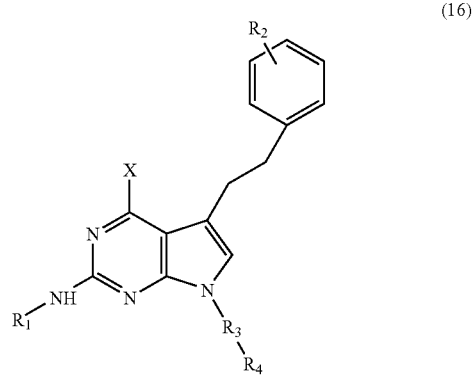

Figure 1:
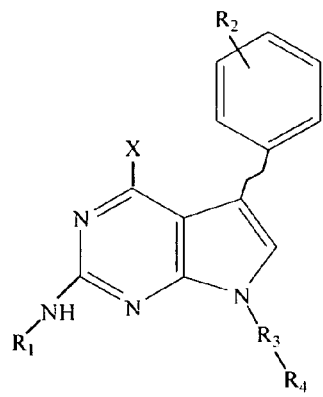
Figure 2A:
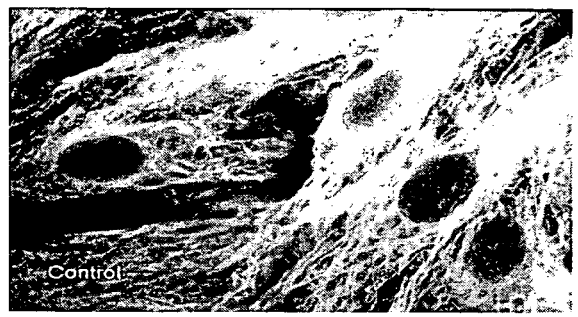
Figure 2B:
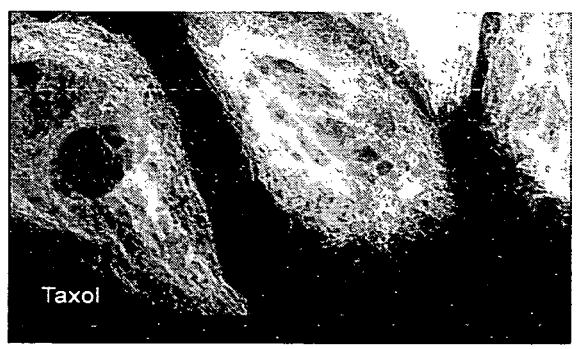
Figure 2C:
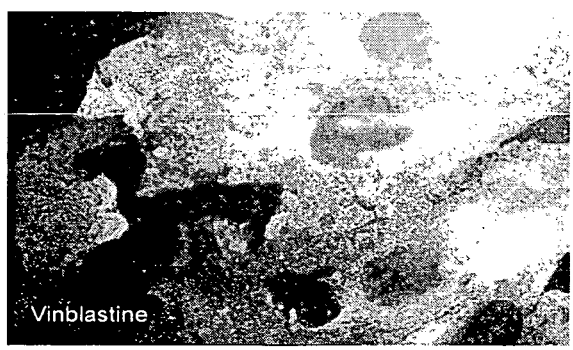
Figure 2D:

where X is selected from the group consisting of lower alkyls, heteroalkyls, substituted or unsubstituted aryls or heteroaryls, arylalkyls, and heteroarylalkyls;

where $R_1$ is selected from the group consisting of hydrogen, lower alkyls, heteroalkyls, substituted or unsubstituted aryls or heteroaryls, arylalkyls, and heteroarylalkyls;

where $R_2$ is selected from the group consisting of hydrogen, lower alkyls, heteroalkyls, alkoxys, substituted or unsubstituted aryls or heteroaryls;

where $R_3$ is selected from the group consisting of zero, lower alkyls, heteroalkyls, alkenyls, and heteroalkenyls; and where $R_4$ is selected from the group consisting of substituted or unsubstituted aryls or heteroaryls, arylalkyls, heteroarylalkyls, and hydrogen. The compound may inhibit mitosis in cells that have developed multidrug resistance due to P-glycoprotein and MRP1, and facilitate the reversal of P-glycoprotein mediated resistance.

35 Claims, 5 Drawing Sheets

| Compound | X | $R_1$ | $R_2$ | $R_3$ | $R_4$ |
|---|---|---|---|---|---|
| 1 | $CH_3$ | H | 3,4,5-triOMe | $CH_2$ | Phenyl |
| 2 | $CH_3$ | H | 4-OMe | $CH_2$ | Phenyl |
| 3 | $CH_3$ | H | 3-OMe | $CH_2$ | Phenyl |
| 4 | $CH_3$ | H | 2-OMe | $CH_2$ | Phenyl |
| 5 | $CH_3$ | H | H | $CH_2$ | Phenyl |
| 6 | $CH_3$ | H | 3,4,5-triOMe | | H |
| 7 | $CH_3$ | H | 4-OMe | | H |
| 8 | $CH_3$ | H | 2-OMe | | H |
| 9 | $CH_3$ | H | H | | H |

Compound 1  (●)
Compound 2  (▲)
Compound 3  (▼)
Compound 4  (♦)
Compound 5  (■)

| | |
|---|---|
| Compound 1 | (●) |
| Compound 2 | (▲) |
| Compound 3 | (▼) |
| Compound 4 | (♦) |
| Compound 5 | (■) |

METHODS FOR TREATING CANCER AND OTHER PATHOLOGICAL PROLIFERATING DISORDERS BY INHIBITING MITOSIS USING PYRROLO[2 3-D]PYRIMIDINES

GOVERNMENT CONTRACT

This work was supported in part by the National Institute of Health, U.S. Department of Health and Human Services under Contract Nos. R01 AI41743 and R01 AI44661.

FIELD OF THE INVENTION

The present invention relates to methods for treating cancer and other pathological proliferating conditions by inhibiting mitosis of cells using pyrrolo[2,3-d]pyrimidines, and more particularly relates to methods for treating these conditions by inhibiting mitosis in cells that have developed multidrug resistance due to P-glycoprotein and MRP1, and facilitating the reversal of P-glycoprotein mediated resistance.

BACKGROUND INFORMATION

Mitosis is the process of nuclear division in eukaryotic cells that produces two daughter cells from one parent cell. The daughter cells and the original parent cell have identical chromosomes and DNA. Cancer is a disease of mitosis. Cancer begins when a single cell is converted from a normal cell to a cancer cell. This is often due to a change in function of one of several genes that normally function to control cell growth. The cancer cells proliferate by repeated, uncontrolled mitosis, in contrast to normal cells which undergo only 20-50 generations of replication and then cease. A tumor is a mass of unhealthy cells that are dividing and growing in an uncontrolled way.

A microtubule is one of the hollow, tube-like filaments found in certain cell components such as the mitotic spindle. Each microtubule is composed of repeating subunits of the protein tubulin. Microtubules aggregate to form spindle fibers. During mitosis, cells use their spindle fibers to line up chromosomes, make copies of them, and divide into new cells with each daughter cell having a single set of chromosomes. Microtubules are the target of commonly used antimitotic or chemotherapeutic drugs, including taxoid drugs such as paclitaxel and docetaxel, vinca alkaloids such as vinblastine, vincristine, and vindesine, colchicine, colcemid, and nocadazol.

Paclitaxel is sold under the name TAXOL. It is a taxoid drug extracted from the bark of the Pacific yew tree that is used for the treatment of ovarian, breast, and Kaposi's sarcoma cancers. Paclitaxel works by blocking a cell's ability to break down the mitotic spindle during mitosis. Paclitaxel binds to the tubulin protein of microtubules, locking the microtubules in place and inhibiting their depolymerization (molecular disassembly). With the mitotic spindle still in place, a cell cannot divide into daughter cells. In contrast, drugs like the vinca alkaloids, colchicine, colcemid, and nocadazol block mitosis by keeping the mitotic spindle from being formed in the first place. These drugs bind to tubulin and inhibit polymerization, preventing cells from making the spindles they need to move chromosomes around as they divide.

Unfortunately, many human cancers are either completely resistant to chemotherapy or respond only transiently, after which they are no longer affected by commonly used antimitotic agents. This phenomenon is known as multidrug resistance (MDR) and is inherently expressed by some tumor types while others acquire MDR after exposure to chemotherapy. P-glycoprotein (PGP), also known as MDR1, is a 170 kD membrane-bound protein which has been implicated as a primary cause of MDR in tumors. PGP is a member of the ATP-binding cassette (ABC) transport protein superfamily. PGPs are efflux transporters found in the gut, gonads, kidneys, biliary system, brain, and other organs, which appear to have developed as a mechanism to protect the body from harmful substances. PGPs transport certain hydrophobic substances, including substances that are clinically therapeutic, into the gut, out of the brain, into urine, into bile, out of the gonads, and out of other organs. MRP1 is another ABC transport protein that is associated with MDR in tumors. MRP1 is a 190 kD integral membrane protein that serves a similar purpose as PGP.

Thus, there exists a need for a method of treatment that employs an antimitotic or antitumor agent capable of inhibiting mitosis in a wide variety of cells, including cells that are subject to MDR, particularly PGP- or MRP1-mediated MDR. There also exists a need for a method of treatment that employs an antimitotic or antitumor agent capable of restoring the sensitivity of a tumor to antimitotic agents following the onset of MDR.

SUMMARY OF THE INVENTION

The present invention provides methods for treating cancer and other pathological proliferating disorders by inhibiting mitosis using pyrrolo[2,3-d]pyrimidines having the general formula (16):

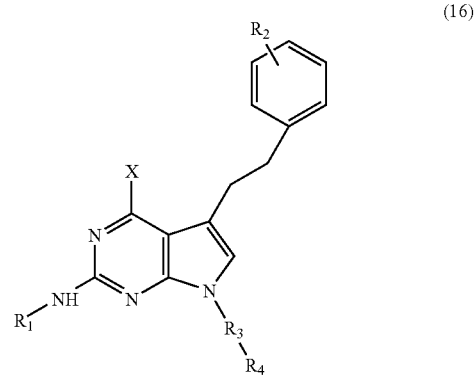

where X is selected from the group consisting of a lower alkyl group a heteroalkyl group, a substituted or unsubstituted aryl group, a substituted or unsubstituted heteroaryl group, an arylalkyl group, and a heteroarylalkyl group;

where $R_1$ is selected from the group consisting of hydrogen, a lower alkyl group, a heteroalkyl group, a substituted or unsubstituted aryl group, a substituted or unsubstituted heteroaryl group, an arylalkyl group, and a heteroarylalkyl group;

where $R_2$ is selected from the group consisting of hydrogen, a lower alkyl group, a plurality of lower alkyl groups, a heteroalkyl group, a plurality of heteroalkyl groups, an alkoxy group, a plurality of alkoxy groups, a substituted or unsubstituted aryl group, a plurality of substituted or unsubstituted aryl groups, a substituted or unsubstituted heteroaryl group, and a plurality of substituted or unsubstituted heteroaryl groups;

where $R_3$ is selected from the group consisting of zero, a lower alkyl group, a heteroalkyl group, an alkenyl group, and a heteroalkenyl group; and where $R_4$ is selected from the group consisting of a substituted or unsubstituted aryl group, a substituted or unsubstituted heteroaryl group, an arylalkyl group, a heteroarylalkyl group, and hydrogen, and $R_4$ is hydrogen when $R_3$ is zero.

Compounds that are covered under formula (16) may be used to inhibit mitosis in cells that are associated with a variety of conditions, including but not limited to melanoma, leukemia, colon cancer, prostate cancer, lung cancer, pancreatic cancer, ovarian cancer, renal cancer, breast cancer, brain cancer, and Kaposi's sarcoma cancer. These compounds are particularly effective at inhibiting mitosis in cells that demonstrate multidrug resistance due to P-glycoprotein and/or MRP1. In addition to inhibiting mitosis, compounds covered under formula (16) may enhance the potency of other treatment agents (e.g., chemotherapeutic agents) by facilitating the reversal of multidrug resistance due to P-glycoprotein. This MDR reversal can restore the sensitivity of cancerous tumors to chemotherapy treatment. Thus, compounds covered under formula (16) may be used alone or in conjunction with additional treatment or chemotherapeutic agents, including but not limited to paclitaxel, docetaxel, the vinca alkaloids, colchicine, colcemid, cisplatin, and nocadazol.

An aspect of the present invention is to provide a method of treating cancer and other pathological proliferating conditions, the method comprising inhibiting mitosis by administering an effective amount of at least one pyrrolo[2,3-d]pyrimidine compound having formula (16) as described hereinabove.

Another aspect of the present invention is to provide a method of treating cancer and other pathological proliferating conditions, the method comprising administering an effective amount of at least one pyrrolo[2,3-d]pyrimidine compound having formula (16) as described hereinabove, and administering an effective amount of an additional chemotherapeutic agent.

An object of the present invention is to provide a novel method of treating cancer by inhibiting mitosis using pyrrolo[2,3-d]pyrimidine compounds.

Another object of the present invention is to provide a method of treating cancerous cells that demonstrate multidrug resistance to antimitotic agents.

A further object of the present invention is to provide a method of restoring a tumor's sensitivity to chemotherapeutic agents following the onset of MDR.

Another object of the present invention is to provide a method of enhancing the potency or effectiveness of commonly used chemotherapeutic agents by administering pyrrolo[2,3-d]pyrimidine compounds along with the chemotherapeutic agents.

A further object of the present invention is to achieve a synergistic effect by administering pyrrolo[2,3-d]pyrimidine compounds along with the chemotherapeutic agents.

These and other aspects of the present invention will become more readily apparent from the following detailed description and appended claims.

TABLES

Table 1 shows tumor cell inhibitory activity ($GI_{50}$) for a pyrrolo[2,3-d]pyrimidine compound in accordance with an embodiment of the present invention.

Table 2 presents NCI COMPARE analysis data for a pyrrolo[2,3-d]pyrimidine compound in accordance with an embodiment of the present invention.

Table 3 presents the cytotoxicity of several pyrrolo[2,3-d]pyrimidine compounds in accordance with embodiments of the present invention.

Table 4 presents the effects of P-glycoprotein and MRP1 on drug sensitivity.

Table 5 shows the effects of a pyrrolo[2,3-d]pyrimidine compound and antimicrotubule drugs on the cell cycle distribution of an NCI tumor cell line.

FIGURES

FIG. 1 depicts various analogs of a pyrrolo[2,3-d]pyrimidine compound in accordance with embodiments of the present invention.

FIGS. 2a-d present pictorial representations of the microtubule structure of a tumor cell line following treatment with antimitotic agents.

Figure 3A:
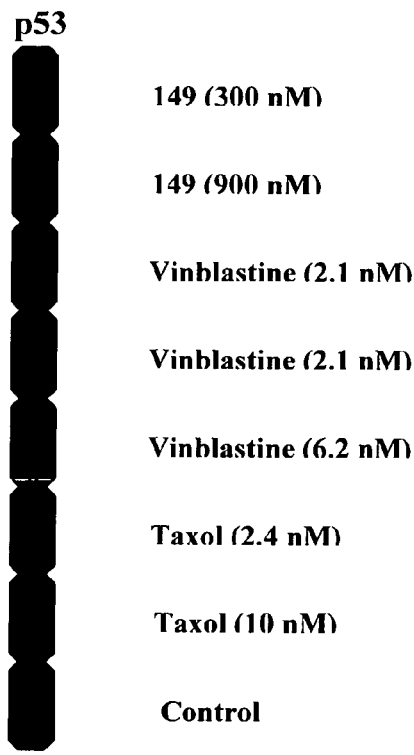
Figure 3B:
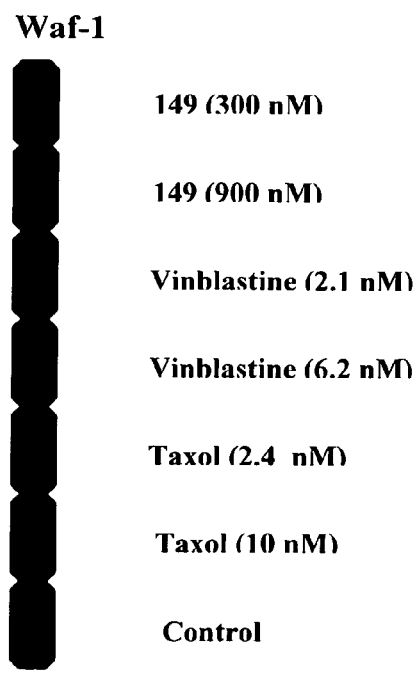

FIGS. 3a-b present the Western blot analyses for expression of p53 and Waf-1, respectively, in a tumor cell line.

Figure 4A:
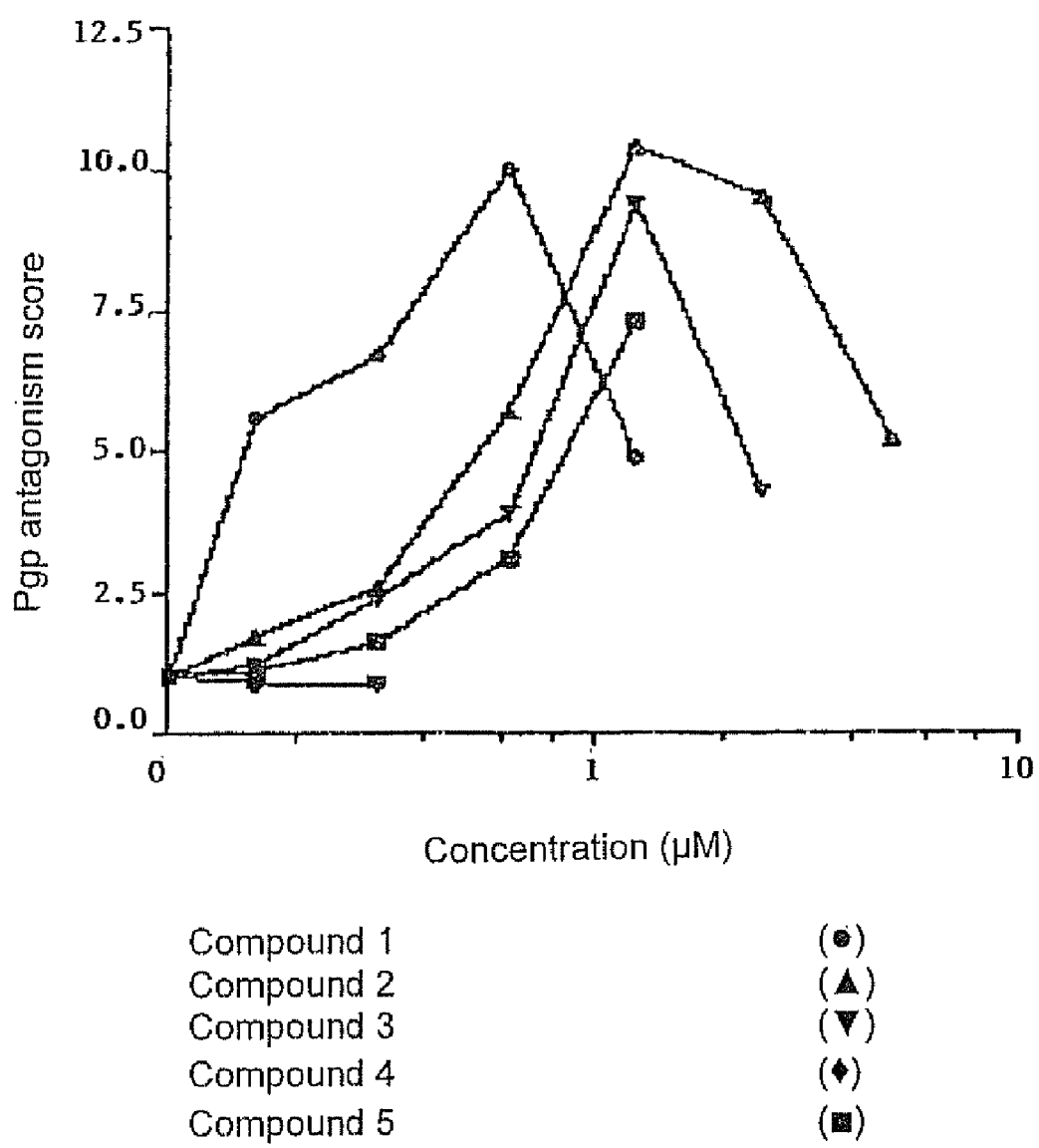
Figure 4B:
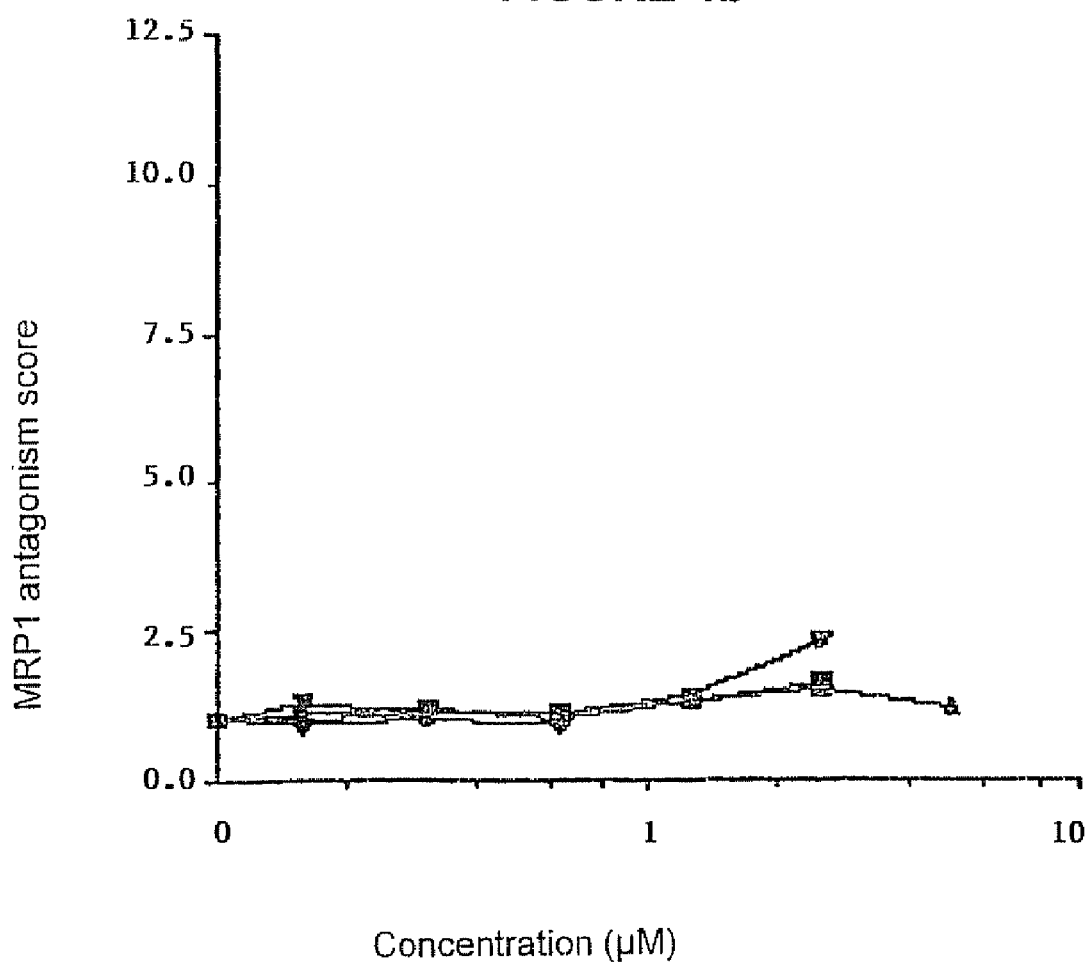

FIGS. 4a-b present graphs of antagonism score versus concentration for P-glycoprotein and MRP1, respectively.

DETAILED DESCRIPTION OF THE PREFERRED EMBODIMENTS

As used herein, the term "patient" refers to members of the animal kingdom including but not limited to human beings.

As used herein, the term "effective amount" refers to that amount of any of the present compounds required to bring about a desired effect in a patient. The desired effect will vary depending on the cancer or illness being treated. On its most basic level, an effective amount is that amount needed to inhibit mitosis or to facilitate the reversal of multidrug resistance. Any amount of inhibition or reversal of multidrug resistance will yield a benefit to a patient and is therefore within the scope of the invention.

It will be appreciated that the effective amount will vary from patient to patient depending on such factors as the cancer or condition being treated, the severity of the cancer or condition, the general health and age of the patient, the size of the patient being treated, the patient's ability to mount an immune response, and the like. The determination of an effective amount for a given patient is within the skill of one practicing in the art. Typically an effective amount will be determined by evaluating potency in standard ex vivo cellular systems, followed by preclinical and clinical in vivo assessment.

The present invention provides methods for treating cancer and other pathological proliferating conditions by inhibiting mitosis using pyrrolo[2,3-d]pyrimidines having the general formula (16):

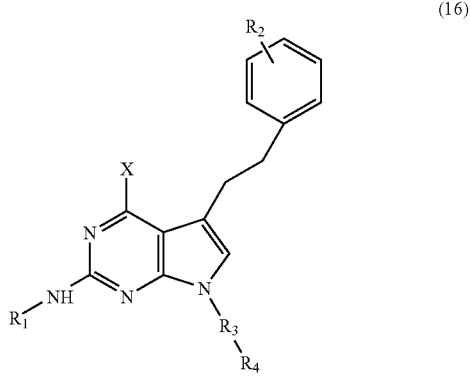

where X is selected from the group consisting of a lower alkyl group, a heteroalkyl group, a substituted or unsubstituted aryl group, a substituted or unsubstituted heteroaryl group, an arylalkyl group, and a heteroarylalkyl group;

where $R_1$ is selected from the group consisting of hydrogen, a lower alkyl group, a heteroalkyl group, a substituted or unsubstituted aryl group, a substituted or unsubstituted heteroaryl group, an arylalkyl group, and a heteroarylalkyl group;

where $R_2$ is selected from the group consisting of hydrogen, a lower alkyl group, a plurality of lower alkyl groups, a heteroalkyl group, a plurality of heteroalkyl groups, an alkoxy group, a plurality of alkoxy groups, a substituted or unsubstituted aryl group, a plurality of substituted or unsubstituted aryl groups, a substituted or unsubstituted heteroaryl group, and a plurality of substituted or unsubstituted heteroaryl groups;

where $R_3$ is selected from the group consisting of zero, a lower alkyl group, a heteroalkyl group, an alkenyl group, and a heteroalkenyl group; and where $R_4$ is selected from the group consisting of a substituted or unsubstituted aryl group, a substituted or unsubstituted heteroaryl group, an arylalkyl group, a heteroarylalkyl group, and hydrogen, and $R_4$ is hydrogen when $R_3$ is zero.

Compounds that are covered under formula (16) may be used to inhibit mitosis in cells and tumors that are associated with a variety of conditions, including but not limited to melanoma, leukemia, colon cancer, prostate cancer, lung cancer, pancreatic cancer, ovarian cancer, renal cancer, breast cancer, brain cancer, and Kaposi's sarcoma cancer. The compounds may inhibit mitosis by binding to tubulin or tubulin-binding proteins, and hindering the polymerization of microtubules and the formation of mitotic spindles (i.e., the pyrimidines may behave like the vinca alkaloids or colchicine). Compounds covered under formula (16) are particularly effective at inhibiting mitosis in cells that demonstrate multidrug resistance due to P-glycoprotein and/or MRP1. In addition to inhibiting mitosis, the compounds may enhance the potency of other treatment agents (e.g., chemotherapeutic agents) by facilitating the reversal of multidrug resistance, particularly multidrug resistance due to P-glycoprotein. In this way, the compounds may partially or completely restore the sensitivity of resistant tumors to chemotherapy treatment. Thus, compounds covered under formula (16) may be used alone or in conjunction with additional treatment or chemotherapeutic agents, for example, paclitaxel, docetaxel, the vinca alkaloids, colchicine, colcemid, cispiatin, or nocadazol.

As used herein, the term "lower alkyl" group refers to those lower alkyl groups having one to about six carbon atoms, such as for example methyl, ethyl, propyl, butyl, pentyl, hexyl, cyclopropyl, cyclobutyl, cyclohexyl, cyclopropylmethyl, or cyclobutylmethyl groups. Alkyl groups sharing one to about six carbon atoms are preferred. These lower alkyl groups may be straight chain, branched chain, or cyclic (alicyclic hydrocarbon) arrangements. The carbon atoms of these straight chain, branched chain, or cyclic arranged alkyl groups may have one or more substituents for the hydrogens attached to the carbon atoms. As used herein, the term "alkenyl" group refers to those groups of unsaturated hydrocarbons that contain at least one atom-to-atom double bond; for example, $C=C$. The alkenyl group can occur as a chain or bridge.

As used herein, the terms "heteroalkyl" and "heteroalkenyl" will be used to refer to alkyl or alkene chains from about one to four atoms where one or more of the carbons has been replaced with nitrogen, oxygen, or sulfur. Thus, "heteroalkyl" and "heteroalkenyl" groups will include, for example, C—C—N, C—S, S—C, C—O, C—C—O, O—C, N—C—C, N—C=C and other various combinations, as will be apparent to one skilled in the art. The above list is not meant to be exhaustive, and many combinations are contemplated as within the scope of the present invention.

"Aryl" groups, as used herein, will refer to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl, and polyaryl groups, which would have two, three, or more rings, respectively. Thus, suitable aryl groups would include, for example, phenyl, biphenyl, naphthyl, phenanthrene, anthracene groups, and aryl oxyaryl groups. This list is not meant to be exhaustive, and any other aryl groups, as these terms are defined above and commonly understood in the art, are within the scope of the present invention. The aryl groups can be substituted or unsubstituted with any number of substituents including but not limited to a lower alkyl group, a substituted or unsubstituted alkoxy, a substituted or unsubstituted alkoxyaryloxy group, a halogen, an amino acid group, and a carboxylic acid group. Similarly substituted diaryl and triaryl groups are also suitable.

The term "heteroaryl", as used herein, will be used to refer to aromatic ring structures having at least one atom in the ring which is not carbon, such as oxygen, nitrogen, or sulfur. "Heteroaryls" also refers to aromatic ring structures that are part of larger ring structures, such as two or three member ring systems, which may be fused or unfused, in which one of the rings is as described above. Thus, "heteroaryl" can refer to ring systems in which one or more rings contain a heteroatom and one or more rings do not. It will be understood that this list is not meant to be exhaustive, and that any heteroaryl group, as these terms are defined above and commonly understood in the art, are within the scope of the present invention. Examples include but are not limited to pyrroles, thiophenes, furans, imidazoles, and the like, as well as fused ring structures having rings of different sizes, such as benzofurans, indoles, purines, and the like. The heteroaryl groups can be substituted or unsubstituted with any number of substituents including but not limited to a lower alkyl group, a substituted or unsubstituted alkoxy, a halogen, an amino acid group, and a carboxylic acid group.

Also included within the scope of the present invention are cyclic aliphatic (or "alicyclic") groups, as that term is understood in the art, and heterocyclic groups. As used herein, the term "heterocyclic group" will refer to non-aromatic cyclic substituents in which one or more members of the ring is not carbon, for example oxygen, sulfur, or nitrogen.

The terms "arylalkyl" (also referred to as "alkyaryl" or "alkaryl") or "heteroarylalkyl" (also referred to as "alkylheteroaryl") as used herein will refer to groups having an alkyl moiety attached to an aryl or heteroaryl ring. The alkyl moiety is preferably a straight, branched, or cyclic alkyl group having one to about six carbon atoms. This alkyl moiety may also contain oxygen, nitrogen, or sulfur atoms, and can therefore be an alkoxy group. The aryl or heteroaryl moiety of the arylalkyl group is a substituted or unsubstituted aryl or heteroaryl group, as these terms are described above. The substituent may be attached at either the alkyl or the aryl portion of the group. Thus, for example, a benzyl group would be embraced by the term "arylalkyl".

Any of the cyclic compounds described above, such as the aryl, heteroaryl, arylalkyl, heteroarylalkyl, alicyclic, or heterocyclic groups are optionally substituted with one or more substituents as listed above. When multiple substituents are present, they are referred to as a "plurality" of substituents. In the case of more than one substituent, each substituent is independently selected, and may be placed at its own unique position along the ring of the parent compound. For example, if an aryl group such as phenyl has a "plurality" of substituent groups, each substituent may be attached to a different carbon atom on the phenyl ring. In the case of a phenyl group that is substituted with a plurality of methoxy groups, e.g., 3,4,5-triOMe, one methoxy group is attached to the carbon at position 3, one methoxy group is attached to the carbon at position 4, and one methoxy group is attached to the carbon at position 5. The number of substituents attached to the ring may vary, but usually ranges from one to six. The substituents may include alkyl groups having straight or branched chains with up to about six members; substituted or unsubstituted alkoxy groups; halogen groups such as chlorine, bromine, iodine and fluorine; substituted or unsubstituted aryl and heteroaryl groups as described above; amino acid groups; carboxylic acid groups such as benzoic acid; or any other suitable chemical. An "acyl" substituent refers to an organic acid group in which the OH is replaced by some other substituent, and is generally designated as RCO— where R is a $C_{1-6}$ alkyl, $C_{2-6}$ alkenyl, or $C_{2-6}$ alkynyl straight or branched chain group.

As used herein, the terms "aroyl" or "heteroaroyl," such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. "Glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described in formula (16) are contemplated as being within the scope of the present invention.

In a preferred embodiment, X is a lower alkyl group, $R_1$ is hydrogen, $R_2$ is selected from the group consisting of an alkoxy group and a plurality of alkoxy groups, $R_3$ is methylene, and $R_4$ is a phenyl group. (The combination of $R_3$ and $R_4$ represents a benzyl group as the N7 moiety.) According to the in vitro studies discussed below, when $R_2$ is 3,4,5-triOMe, $R_3$ is methylene, and $R_4$ is phenyl, the pyrrolo[2,3-d]pyrimidine compound appears to be a potent antimitotic agent, particularly against antimitotic sensitive and resistant cells. Thus, in a preferred embodiment, X is methylene, $R_1$ is hydrogen, $R_2$ is 3,4,5-triOMe, $R_3$ is methylene, and $R_4$ is a phenyl group. In another embodiment, $R_2$ is preferably equal to 3-OMC and/or 5-OMe because the 3-OMe and 5-OMe groups appear to have more antimitotic effectiveness than the 4-OMe group. When $R_3$ and $R_4$ (i.e., the N7 moiety) are removed from the pyrrolo[2,3-d]pyrimidine compound, there is a significant decrease in antimitotic activity against tumor cells. Therefore, it is preferable to have the $R_3$ and/or $R_4$ groups present because it is preferable to have an N7 moiety present.

When $R_2$ is 2-OMe, $R_3$ is methylene, and $R_4$ is phenyl, the pyrrolo[2,3-d]pyrimidine compound is about 10 times less potent as an antimitotic agent than the 3,4,5-triOMe analog. However, the 2-OMe analog appears to be effective at reversing P-glycoprotein mediated resistance to antimitotics. Thus, in another preferred embodiment, X is methylene, $R_1$ is hydrogen, $R_2$ is 2-OMe, $R_3$ is methylene, and $R_4$ is a phenyl group.

In another preferred embodiment, the compound is a 2,3,4,5-tetraOMe analog, which combines the antimitotic activity of the 3,4,5-triOMe analog with the MDR reversal activity of the 2-OMe analog. In this embodiment, X is methylene, $R_1$ is hydrogen, $R_2$ is 2,3,4,5-tetraOMe, $R_3$ is methylene, and $R_4$ is a phenyl group. Alternatively, a compound in which $R_2$ is 3,4,5-triOMe may be administered with a compound in which $R_2$ is 2-OMe to combine antimitotic activity with MDR reversal.

Compounds that are covered under formula (16) may be contained within a suitable pharmaceutical carrier for administration according to the present methods. "Suitable pharmaceutical carrier" refers to any pharmaceutical carrier that will solubilize the present compounds and will not give rise to compatibility problems and includes any and all solvents, dispersion media, coatings, antibacterial and antifungal agents, isotonic and absorption delaying agents, and the like. The use of such media and agents for pharmaceutical use is well known in the art. Use of any of these media or agents is contemplated by the present invention, absent compatibility problems with the chimeric proteins. Preferred carriers include physiologic saline and 5 percent dextrose.

Compounds that are covered under formula (16) may be delivered by parenteral, oral, or topical administration. It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of pyrrolo[2,3-d]pyrimidine compound to produce the desired effect in association with the pharmaceutical carrier. The specification for the dosage unit forms of the invention are dictated by and directly dependent on the particular compound and the particular effect to be achieved.

Compounds that are covered under formula (16) may also be administered with one or more additional treatment agents, e.g., a chemotherapeutic agent. Suitable candidates for the additional chemotherapeutic agent include but are not limited to paclitaxel, docetaxel, vinca alkaloids, colchicine, colcemid, cisplatin, and nocadazol. The presence of the pyrrolo[2,3-d]pyrimidine compounds will enhance the effectiveness of the chemotherapeutic agent by facilitating the reversal of multidrug resistance, particularly multidrug resistance due to P-glycoprotein, and at least partially restoring the sensitivity of tumors to antimitotic agents. In one embodiment, compounds having formula (16) may be combined with the additional chemotherapeutic agents and administered together, either in the same pharmaceutical carrier, or in different carriers but at generally the same time. In another embodiment, compounds having formula (16) may be administered prior to and separately from the additional chemotherapeutic agents, giving the pyrrolo[2,3-d]pyrimidine compound sufficient time to effectuate the reversal of multidrug resistance. In addition to facilitating the reversal of multidrug resistance, compounds covered under formula (16) will have some effect as antimitotic agents on the tumor.

The administration of a compound having formula (16) along with an additional chemotherapeutic agent may result in a synergistic effect. Synergism occurs when two compounds used together have a greater effect than when the two compounds are used separately. When synergism occurs, it is possible to use less of each compound, thereby decreasing the toxicity of each compound.

EXAMPLES

Example 1

FIG. 1 presents nine compounds that were tested using the National Cancer Institute (NCI) 60 human tumor cell lines.

The cells lines, which represent leukemia, melanoma, and cancers of the lung, colon, brain, ovary, breast, prostate, and kidney, are listed in Table 1.

Compounds 1-9 were tested according to the NCI Developmental Therapeutics Program (DTP) In Vitro Cell Line Screening Project (IVCLSP). Compounds 1-5 included an N7-benzyl moiety, whereas Compounds 6-9 did not include an N7-benzyl moiety. Methodology for testing under the IVCLSP is as follows: The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz.$$

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

Compound 1, the 3,4,5-triOMe analog, inhibited the most tumors in the NCI 60 tumor panel. Table 1 shows the tumor cell inhibitory activity, measured by $GI_{50}$ (nM), for Compound 1. As shown, the $GI_{50}$ values (nM) for the various tumor cell lines ranged from nanomolar to submicromolar levels. $GI_{50}$ represents the concentration of chemical required to reduce the growth of treated cells to half that of untreated (i.e., control) cells. In other words, $GI_{50}$ represents the concentration of chemical required to effectuate 50 percent inhibition of cell growth.

Compound 1 exhibited $GI_{50}$ values of single or two digit nanomolar levels against 16 tumor cell lines, submicromolar levels against 40 tumor cell lines, and micromolar levels against 3 tumor cell lines. Compared to Compound 1, Compound 6 which did not include the N7-benzyl moiety exhibited decreased activity by 100 to 10,000 times against 56 tumor cell lines. This shows the importance of the N7-benzyl moiety in helping the pyrrolo[2,3-d]pyrimidine compounds inhibit tumor cell growth.

Compound 2 (the 4-OMe analog) inhibited the tumor cells at concentrations that were similar to those of Compound 6, indicating the importance of the 3- and/or 5-OMe groups. Compound 3 (the 3-OMe analog), however, showed $GI_{50}$ values in the micromolar range for 8 of the 56 tumor cell lines and a two digit nanomolar level against the renal cancer A498 cell. Compound 4 (the 2-OMe analog) was similar to Compound 3, with $GI_{50}$ values in the micromolar to millimolar range.

Compound 5, a phenyl unsubstituted analog, had $GI_{50}$ values in the millimolar or less range for 52 of the tumor cell lines, with micromolar $GI_{50}$ values for three of the tumor cell lines. Removal of the N7-benzyl group from any of the compounds substantially decreased activity against the NCI 60 tumor panel. The structure-activity-relationship from Compounds 1-9 indicated that the 3,4,5-triOMe substitution along with the presence of the N7-benzyl moiety was important for potent inhibitory activity against tumor cells in culture.

An NCI COMPARE analysis was performed for Compound 1 to elucidate a possible mechanism of action by comparing the responses of the 60 cell lines to known microtubule-targeting agents. Table 2 lists the five agents whose cell type selectivity profile exhibited Pearson correlation coefficients (PCC) that were similar to Compound 1. For microtubule specific compounds, the cell type selectivity profile in tumor growth inhibitory (TGI) levels is highly indicative of the compound's mechanism of action. For a compound to be categorized as a microtubule-targeting agent, it should meet the following requirements: 1) the PCC value should be at least 0.6, and 2) the average $GI_{50}$ should be one µM or less. Compound 1 satisfied both of these requirements, indicating an antitubulin mechanism of action.

Example 2

Compounds 1-5 were also evaluated for cytotoxicity towards the panel of human tumor cell lines identified in Table 3. These cell lines are resistant to anticancer drugs due to overexpression of the transport proteins P-glycoprotein or MRP1. The unsubstituted phenyl ethyl Compound 5 demonstrated $IC_{50}$s ranging from 11 to 18 μM. ($IC_{50}$ is the inhibitory concentration required to effectuate 50 percent inhibition of cell growth.) NCI/ADR cells that overexpress P-glycoprotein and MCF-7VP cells that overexpress MRP1 had $IC_{50}$s slightly higher than the drug-sensitive MCF-7 cells. 4-OMe substitution of the 5-phenyethyl moiety (Compound 2) decreased the cytotoxic potency toward T24 human bladder carcinoma cells, but had little effect on the potency toward the other cell lines. Conversely, a 3-OMe substitution (Compound 3) enhanced the potency toward NCI/ADR cells, and a 2-OMe substitution (Compound 4) substantially increased the potency toward all of the tested cell lines and eliminated any resistance due to overexpression of either P-glycoprotein or MRP1. Submicromolar cytotoxic potency was observed for the 3,4,5-triOMe Compound 1, again regardless of the transporter status of the cells. Clearly the preliminary structure activity studies indicate that the 3,4,5-triOMe substitution is important for potent activity. Among the mono-OMe analogs the 2-OMe is better than the 3-OMe and the 4-OMe. However the unsubstituted phenyl analog is better than a mono 3- or 4-OMe substitution. Thus the triOMe analog, Compound 1, is 10-fold better than Compound 4 (2-OMe) which in turn is about 10-times better than the 3- or 4-OMe and 5-times better than the unsubstituted phenyl analog Compound 5.

Because of the effects of the compounds on microtubules (discussed hereinafter), the cytotoxic activity of Compound 1 was compared with the microtubule-targeting drugs TAXOL (paclitaxel), vinblastine, and vincristine, as shown in Table 4. Although each of these natural product drugs was more potent than Compound 1 in the sensitive cell line, each was subject to tumor cell resistance due to the overexpression of P-glycoprotein. Additionally, overexpression of MRP1 also confers substantial resistance to vincristine. In contrast, the observation that neither P-glycoprotein nor MRP1 affect cell sensitivity to Compound 1 was confirmed. Compound 1 was 35- to 40-fold more potent than the established anticancer drug cisplatin, which is also insensitive to transporter expression by the tumor cells.

Example 3

Because of the morphological effects of Compound 1 on cultured cells and the NCI COMPARE analysis results described above, the effects of vinblastine, TAXOL (paclitaxel) and Compound 1 on microtubule structure were examined. For these studies, A-10 rat smooth muscle cells were used since they grow as flat monolayers that are amenable to imaging. The A-10 cells were treated for 24 hours with EtOH (control), 625 nM TAXOL (paclitaxel), 167 nM vinblastine, and 900 nM of Compound 1. Microtubules were then visualized by indirect immunofluoresence staining with B-tubulin antibodies. FIGS. 2a-d present representative fields for the control, TAXOL (paclitaxel), vinblastine, and Compound 1 ("149"), respectively. None of these compounds affected the morphology of stress fibers composed of microfilaments. Control cells displayed extensive microtubule systems with perinuclear organizing centers. Treatment with TAXOL (paclitaxel) promoted increased staining of microtubule clusters in these cells, while vinblastine caused marked depletion of cellular microtubules. Similarly, Compound 1 caused dose-dependent losses of microtubules in the cells. Like TAXOL (paclitaxel), many cells with aberrant nuclei were observed in cultures treated with Compound 1. Similar loss of microtubules were observed in cultures of NIH/3T3 and MCF-7 cells treated with Compound 1.

Example 4

Flow cytometric analyses were used to assess the effects of Compound 1 and various antimicrotubule drugs on the cell cycle phase distributions of HL-60 human promyelocytic leukemia cells. Table 5 summarizes the results of this experiment. The percentage of cells in the $G_2$/M phases were increased approximately 2-fold by treatment of the cells for 24 hours with either TAXOL (paclitaxel), vinblastine, colchicine, or Compound 1. Increasing the incubation time to 48 hours did not substantially increase the percentage of cells arrested in $G_2$/M for any of the compounds; however, the percentage of subdiploid cells was increased in each sample indicating the induction of apoptosis by these compounds.

To further characterize the cell cycle effects of Compound 1 on human tumor cells, MCF-7 cells were treated for 24 hours with various concentrations of Compound 1, vinblastine, or TAXOL (paclitaxel). Cells were then harvested, lysed, and analyzed for levels of expression of p53 and WAF1 by Western Blot analyses. The Western Blot analyses for p53 and WAF1 are displayed in FIGS. 3a and 3b, respectively. Compound 1 is identified as "149" in these figures. Arrest of these cells in $G_2$/M by antimicrotubule drugs has previously been demonstrated to correlate with increased expression of these proteins. As predicted, treatment with TAXOL (paclitaxel) or vinblastine resulted in marked increases in the levels of expression of both p53 and WAF1. Similarly, treatment with Compound 1 induced the expression of both of these proteins. None of these treatments affected the expression of bcl-2 or P-tubulin in the MCF-7 cells.

Example 5

Studies described above indicated that expression of P-glycoprotein or MRP1 does not confer resistance to the cytotoxic effects of the compounds. To determine if this is due to inhibition of drug transport activity by these proteins, the effects of these compounds on P-glycoprotein were further characterized. The effects of the compounds on the sensitivity of NCI/ADR cells to vinblastine and of MCF-7/VP cells to vincristine were examined to evaluate antagonism of P-glycoprotein and MRP1, respectively. FIGS. 4a-b present graphs of antagonism score versus concentration for P-glycoprotein and MRP1, respectively.

As shown in FIG. 4a, NCI/ADR cells were treated with the indicated concentrations of Compound 5 (■), Compound 2 (▲), Compound 3 (▼), Compound 4 (♦) or Compound 1 (●) either in the absence or the presence of 50 nM vinblastine. The Pgp antagonism score is calculated as the percentage survival of cells in the absence of vinblastine/percentage survival in the presence of vinblastine. As shown in FIG. 4b, MCF-7/VP cells were treated as indicated above in the absence or presence of 1 nM vincristine. The MRP1 antagonism score is calculated as the percentage survival of cells in the absence of vincristine/percentage survival in the presence of vincristine. In both cases, a value of 1 indicates that the compound has no affect on drug sensitivity while increasing values indicate increasing antagonism of the transport protein. Concentrations of Compounds 1-5 above their $IC_{50}$ toward MCF-7 cells are not indicated. Data for one of three similar experiments is shown.

As indicated in FIG. 4a, increasing doses of either Compound 2, 3, 4 or 5 caused dose-dependent sensitization of NCI/ADE cells to vinblastine indicating inhibition of P-glycoprotein. Compound 4 was approximately 10-fold more potent than the others in reversing P-glycoprotein-mediated resistance. Apparent decreases in this activity by high doses of the compounds are due to direct cytotoxicity of the compound, thereby lowering the ratio of survival in the absence of vinblastine relative to survival in the presence of vinblastine. Compound 1 was significantly more cytotoxic than the others in the series, but had no affect on P-glycoprotein at doses below its $IC_{50}$. In contrast with the marked effects on P-glycoprotein-mediated resistance, none of the compounds affected the ability of vincristine to kill MCF-7/VP cells, indicating that they are ineffective in blocking the actions of MRP1.

Overall, these data demonstrate that ortho-OMe substitution of the 5-phenethyl moiety of this series greatly enhances its ability to inhibit P-glycoprotein, whereas further substitution may negate this effect but enhance direct cytotoxicity. Thus, the 2-OMe substituted Compound 4 is most conducive to inhibition of P-glycoprotein for reversing P-glycoprolein-mediated resistance to vinblastine. Whether Compound 1 also has this attribute cannot be determined due to its high cytotoxicity. However, since Compound 1 at concentrations below its $IC_{50}$ had no effect on P-glycoprotein-mediated resistance, it is possible that it is not a substrate for Pgp but does not inhibit Pgp like Compounds 2-5 do.

Whereas particular embodiments of this invention have been described above for purposes of illustration, it will be evident to those skilled in the art that numerous variations of the details of the present invention may be made without departing from the invention as defined in the appended claims.

TABLE 1

| PANEL/CELL LINE | $GI_{50}$ |
|---|---|
| Leukemia | |
| CCRF-CEM | 58.0 |
| HL-60(TB) | 64.7 |
| K-562 | 84.6 |
| MOLT-4 | 285 |
| RPMI-8226 | 439 |
| SR | 31.4 |
| NSCLC | |
| A549/ATCC | 173 |
| EKVX | 424 |
| HOP-92 | 467 |
| NCI-H226 | 195 |
| NCI-H23 | 278 |
| NCI-H322M | 581 |
| NCI-H460 | 162 |
| NCI-H522 | 47.7 |
| Colon Cancer | |
| COLO 205 | 190 |
| SK-MEL-2 | 381 |
| SK-MEL-28 | >1000 |
| SK-MEL-5 | 61.1 |
| UACC-257 | 80.2 |
| UACC-62 | 39.9 |
| Ovarian cancer | |
| IGROVI | 61.1 |
| OVCAR-3 | 28.8 |
| OVCAR-4 | 821 |
| OVCAR-5 | >1000 |
| OVCAR-8 | 364 |
| SK-OV-3 | 506 |
| Renal Cancer | |
| 786-0 | 254 |
| A498 | 136 |

TABLE 1-continued

| PANEL/CELL LINE | $GI_{50}$ |
|---|---|
| ACHN | 728 |
| CAKI-1 | 366 |
| HCC-2998 | 317 |
| HCT-116 | 286 |
| HCT-15 | 127 |
| HT29 | 281 |
| KM12 | 194 |
| SW-620 | 236 |
| CNS Cancer | |
| SF-268 | 669 |
| SF-295 | 41.8 |
| SF-539 | 74.5 |
| SNB-19 | 273 |
| SNB-75 | 358 |
| U251 | 144 |
| Melanoma | |
| LOX IMVI | 250 |
| MALME-3M | 283 |
| M14 | 77.0 |
| RXF 393 | 134 |
| SN12C | 537 |
| TKIO | 961 |
| UO-31 | 347 |
| Prostate Cancer | |
| PC-3 | 47.9 |
| DU-145 | 224 |
| Breast Cancer | |
| MCF7 | 118 |
| NCI/ADR-RES | 145 |
| MDA-MB-231/ATCC | 595 |
| HS 578T | 283 |
| MDA-MB-435 | 10.1 |
| MDA-N | <10.0 |
| BT-549 | >1000 |
| T-47D | 563 |

TABLE 2

Compare Analysis Data for Compound 1

| Drug | Correlation Coefficient |
|---|---|
| vinblastine sulfate | 0.748 |
| Paclitaxel | 0.680 |
| Rhizoxin | 0.677 |
| Maystansine | 0.663 |
| vincristine sulfate | 0.635 |

TABLE 3

Cytotoxicity of Compounds 1-5

| Compound | T24 | MCF-7 | NCI/ADR | MCF-7/VP |
|---|---|---|---|---|
| 1 | 0.28 ± 0.10 | 0.30 ± 0.16 | 0.25 ± 0.12 | 0.25 ± 0.16 |
| 2 | 31.7 ± 1.7 | 13.0 ± 3.5 | 21.7 ± 4.4 | 22.7 ± 3.7 |
| 3 | 25.0 ± 2.9 | 8.0 ± 3.5 | 5.7 ± 0.7 | 22.0 ± 4.2 |
| 4 | 2.5 ± 0.3 | 2.3 ± 0.6 | 2.7 ± 0.4 | 2.6 ± 0.1 |
| 5 | 12.7 ± 2.3 | 10.7 ± 4.7 | 18.2 ± 7.4 | 118.3 ± 6.0 |

Note:
Values are expressed as μM and represent the mean ± SEM for 3 experiments.

TABLE 4

Effects of P-glycoprotein and MRP1 on drug sensitivity

| Drug | MCF-7 | NCI/ADR | Resistance | MCF-7/VP | Resistance |
|---|---|---|---|---|---|
| TAXOL (paclitaxel) (nM) | 2.5 ± 0.6 | 2700 ± 500 | 1080 | 2.8 ± 0.6 | 1.1 |
| Vinblastine (nM) | 2.8 ± 0.5 | >375 | >134 | 3.0 ± 0.6 | 1.1 |
| Vincristine (nM) | 0.6 ± 0.1 | 100 | 167 | 9.3 ± 1.4 | 15.5 |
| Cisplatin (µM) | 11.5 ± 4.1 | 12.2 ± 4.2 | 1.1 | 7.0 ± 2.9 | 0.6 |
| Compound 1 (µM) | 0.28 ± 0.01 | 0.35 ± 0.04 | 1.3 | 0.18 ± 0.01 | 0.6 |

Note:
Values are expressed in µM and represent the mean ± SEM for 3 experiments.

TABLE 5

Effects of Compound 1 and antimicrotubule drugs on the cell cycle distribution of HL-60 cells

| Treatment | $G_0/G_1$ | S | $G_2/M$ |
|---|---|---|---|
| Control | 78.5 ± 0.0 | 16.6 ± 0.2 | 4.9 ± 0.2 |
| TAXOL (paclitaxel) | 67.3 ± 0.4 | 22.2 ± 0.4 | 10.5 ± 0.1 |
| Vinblastine | 83.3 ± 1.3 | 6.6 ± 1.6 | 10.1 ± 0.3 |
| Colchicine | 84.1 ± 0.7 | 4.0 ± 1.4 | 11.9 ± 0.3 |
| Compound 1 | 80.0 ± 2.4 | 10.3 ± 2.0 | 9.7 ± 0.4 |

What is claimed is:

1. A method of treating cancer, the method comprising inhibiting mitosis by administering an effective amount of at least one compound having the formula (16) to a patient with a leukemia or melanoma cell line or a cancer of the lung, colon, brain, ovary, breast, prostate, or kidney:

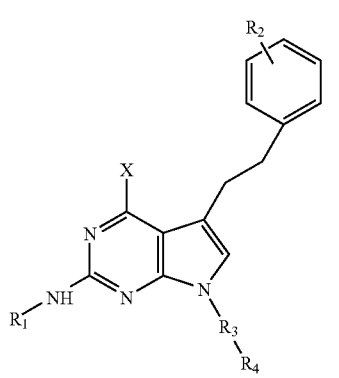

(16)

wherein X is a lower alkyl group;
wherein $R_1$ is hydrogen;
wherein $R_2$ is selected from the group consisting of an alkoxy group and a plurality of alkoxy groups, wherein each of said alkoxy group or groups is a methoxy group;
wherein $R_3$ is methylene; and
wherein $R_4$ is a phenyl group.

2. The method of claim 1, wherein X is methyl.

3. The method of claim 2, wherein $R_2$ is 3, 4, 5-triOMe.

4. The method of claim 2, wherein $R_2$ is selected from the group consisting of 3-OMe and 2-OMe.

5. The method of claim 1, wherein said compound is administered by a method selected from the group consisting of parenteral administration, oral administration, and topical administration.

6. The method of claim 1, wherein said compound is incorporated in a suitable pharmaceutical carrier.

7. The method of claim 6, wherein said pharmaceutical carrier is selected from the group consisting of physiologic saline and 5 percent dextrose.

8. The method of claim 1, wherein said compound inhibits polymerization of microtubules and the formation of mitotic spindles.

9. The method of claim 1, wherein said compound inhibits mitosis in cells that have multidrug resistance.

10. The method of claim 9, wherein said multidrug resistance is due to P-glycoprotein.

11. The method of claim 9, wherein said multidrug resistance is due to MRP1.

12. The method of claim 1, wherein said compound facilitates reversal of multidrug resistance.

13. The method of claim 12, wherein said multidrug resistance is due to P-glycoprotein.

14. The method of claim 1, further comprising administering an effective amount of at least one additional chemotherapeutic agent.

15. The method of claim 14, wherein said additional chemotherapeutic agent is selected from the group consisting of paclitaxel, docetaxel, vinca alkaloids, colchicine, colcemid, cisplatin, and nocadazol.

16. A method of treating cancer, the method comprising:
administering an effective amount of at least one compound having the formula (16) to a patient with a leukemia or melanoma cell line or a cancer of the lung, colon, brain, ovary, breast, prostate, or kidney:

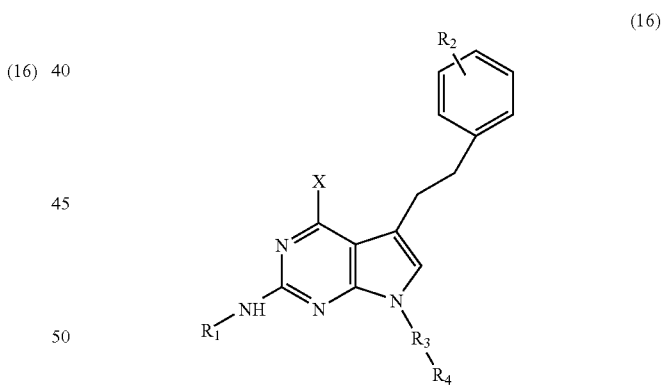

(16)

wherein X is a lower alkyl group;
wherein $R_1$ is hydrogen;
wherein $R_2$ is selected from the group consisting of an alkoxy group and a plurality of alkoxy groups, wherein each of said alkoxy group or groups is a methoxy group;
wherein $R_3$ is methylene; and
wherein $R_4$ is a phenyl group; and
administering an effective amount of an additional chemotherapeutic agent.

17. The method of claim 16, wherein X is methyl.

18. The method of claim 17, wherein $R_2$ is 2-OMe.

19. The method of claim 17, wherein $R_2$ is 2,3,4,5-tetraOMe.

20. The method of claim 17, wherein a compound having $R_2$ equal to 2-OMe is administered along with a compound having $R_2$ equal to 3,4,5-triOMe.

21. The method of claim 16, wherein said additional chemotherapeutic agent is selected from the group consisting of paclitaxel, docetaxel, vinca alkaloids, colchicine, colcemid, cisplatin, and nocadazol.

22. The method of claim 16, wherein said compound is incorporated in a suitable pharmaceutical carrier.

23. The method of claim 22, wherein said pharmaceutical carrier is selected from the group consisting of physiologic saline and 5 percent dextrose.

24. The method of claim 16, wherein said compound is administered by a method selected from the group consisting of parenteral administration, oral administration, and topical administration.

25. The method of claim 16, wherein said additional chemotherapeutic agent is administered by a method selected from the group consisting of parenteral administration, oral administration, and topical administration.

26. The method of claim 16, wherein said multidrug resistance is due to P-glycoprotein.

27. The method of claim 16, wherein said multidrug resistance is due to MRP1.

28. The method of claim 16, wherein said compound facilitates reversal of P-glycoprotein mediated multidrug resistance.

29. The method of claim 16, wherein said compound enhances the antimitotic effectiveness of said additional chemotherapeutic agent.

30. The method of claim 16, wherein said compound and said additional chemotherapeutic agent are administered simultaneously.

31. The method of claim 16, wherein said compound is administered prior to and separately from said additional chemotherapeutic agent.

32. The method of claim 16, wherein said compound and said additional chemotherapeutic agent achieve a synergistic effect.

33. The method of claim 1, wherein $R_2$ is 3,4,5-triOMe.

34. The method of claim 16, wherein $R_2$ is 3,4,5-triOMe.

35. The method of claim 17, wherein $R_2$ is 3,4,5-triOMe.

* * * * *